United States Patent [19]

Rosenfeld et al.

[11] Patent Number: 5,063,275

[45] Date of Patent: Nov. 5, 1991

[54] METHOD AND APPARATUS FOR GAS ANALYSIS

[75] Inventors: Elieser Z. Rosenfeld; Lewis Coleman, both of Jerusalem, Israel

[73] Assignee: Spegas Industries Ltd., Jerusalem, Israel

[21] Appl. No.: 541,637

[22] Filed: Jun. 21, 1990

[30] Foreign Application Priority Data

Jun. 25, 1989 [IL]  Israel .................................. 90744

[51] Int. Cl.⁵ .............................................. G01N 21/61
[52] U.S. Cl. ..................................... 250/343; 250/345; 356/433; 356/434; 356/435; 356/437
[58] Field of Search ................. 250/345, 343; 356/434, 356/433, 435, 437

[56] References Cited

U.S. PATENT DOCUMENTS

| | | | |
|---|---|---|---|
| 4,346,296 | 8/1982 | Passaro et al. ....................... | 250/343 |
| 4,355,234 | 10/1982 | Fertig et al. ........................... | 250/343 |
| 4,755,675 | 7/1988 | Rosenfeld et al. ................... | 250/343 |
| 4,780,613 | 10/1988 | Berstein et al. ....................... | 250/343 |

FOREIGN PATENT DOCUMENTS 541113   1/1977   U.S.S.R. .............................. 250/343

OTHER PUBLICATIONS

D. W. Hill and T. Powell, "Non-Dispersive Infra-Red Gas Analysis in Science, Medicine and Industry." (Plenum Press, New York, 1968), pp. 30-33, 42-55.

*Primary Examiner*—Constantine Hannaher
*Attorney, Agent, or Firm*—Scully, Scott, Murphy & Presser

[57] ABSTRACT

There is provided a gas analyzer, including a radiation source, an analytical space through which passes the gas to be analyzed, at least one detector for detecting the intensity of radiation passing through the space, apparatus for facilitating the alternating introduction, into the space, of the gas to be analyzed and a reference gas having a concentration located at least in the upper half of the range of concentrations to be measured by the gas analyzer. The analyzer further includes processing apparatus, having a memory device, to process signals originating in the detector, the memory device adapted to store in a first mode of operation, signals representing instantaneous intensity values of the detected source and, in a second mode of operation, to store signals representing intensity values obtained when the analytical space is filled with the reference gas, a circuit for comparing the instantaneous values with the reference value, and an indicator device for indicating concentration. A method for analyzing gases to establish their concentration is also provided.

10 Claims, 5 Drawing Sheets

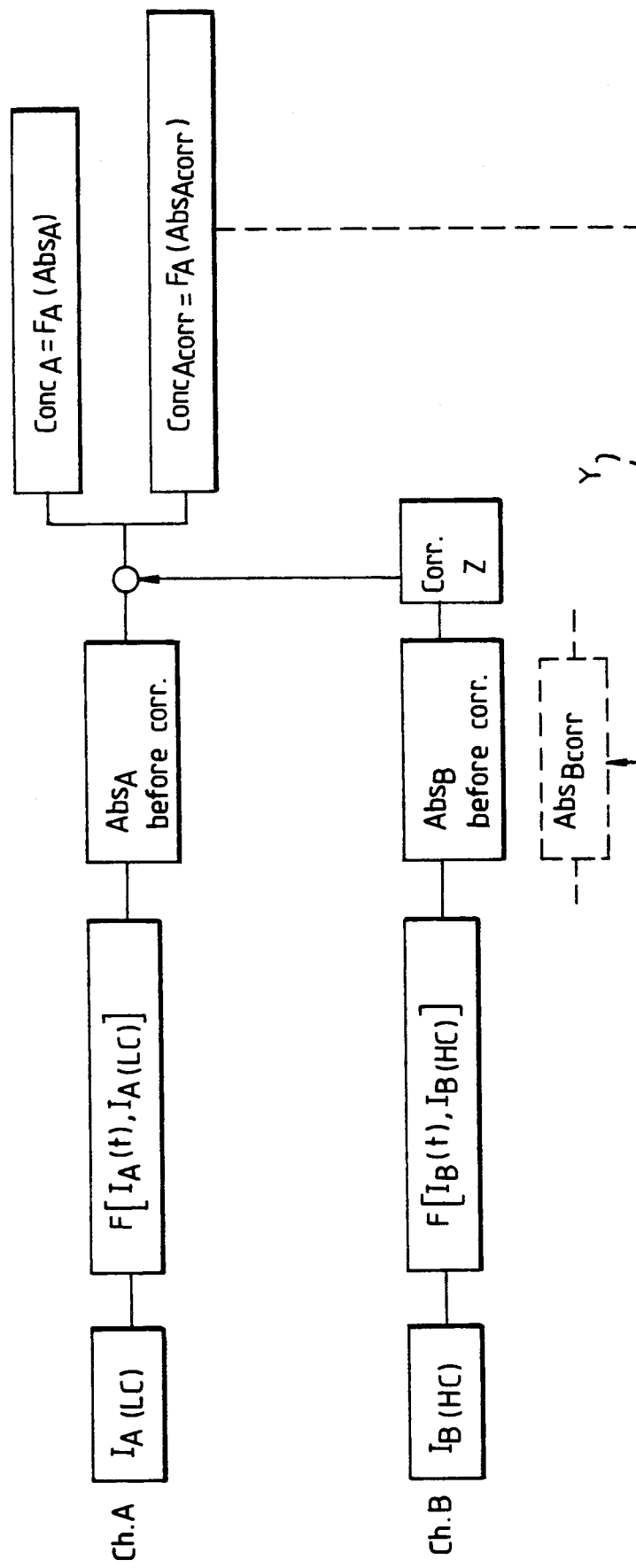

METHOD AND APPARATUS FOR GAS ANALYSIS

The present invention relates to a method for analyzing gases to establish their concentration, e.g., $CO_2$-concentration in closed spaces or in breath.

It further relates to a gas analyzer to establish such concentrations.

While the use of the method and the device according to the invention is by no means limited to medical applications thereof, explanations given will be largely based on examples from this field. It will be appreciated that this is only for illustrative purposes and is not meant to restrict the scope of the invention.

Measurement of gas concentration by optical-absorption methods is well-known (Hill & Powell, "Non-Dispersive Infrared (NDIR) Gas Analysis in Science". Plenum Press, 1968, U.S. Pat. No. 4,346,296 and U.S. Pat. No. 4,355,234).

In medical use, non-dispersive infrared (NDIR) gas analysis has been employed in many fields of gas detection, among others also for capnometry—the measurement of $CO_2$ concentration in the breath. Monitoring respiration is a very valuable method in patient care and diagnosis. In case of surgery, in the intensive Care Units, or in other life-threatening situations, it may be vital to have reliable information on oxygen metabolism in form of a capnogram.

Measurement of gas concentration by optical absorption is based on the Beer-Lambert Law of Optical Absorption, according to which $$I = I_o e^{-kcs}$$

where $k$ = extinction coefficient
$c$ = concentration of gas
$s$ = optical path length of the analytical space
$I_o$ = Intensity of light source at $c=0$,
therefore, in order to calculate $c$ (at constant $k,s$), knowledge of $I$ and $I_o$ is required. This is generally achieved in two ways:

a) Single channel systems $I_o$ is measured during time periods when a known zero-gas is present in the optical path of the measuring chamber (cuvette).

This can be done by periodically injecting zero gas into the analytical space (especially in side-stream sampling systems) or, by regarding the inhalation part of the breath cycle when $CO_2$ concentration is negligibly low as a zero-base period and equating $I(\text{inhalation}) = I_o$. This method is capable of correcting for window shading or of detecting the presence of water in the cuvette (analytical space), but it will fail when the condition of rebreathing of $CO_2$ occurs. This condition of inhaling a much higher $CO_2$ content than ambient may happen voluntarily during the weaning-off procedures from artificial ventilators or accidentally when the $CO_2$ scrubber in the anesthesia machines fails. In both cases, dangerously false results of the $CO_2$ concentration determination will occur.

b) Two-Channel systems

Another way to determine $I_o$ is the use of a two-channel system. One channel is sensitive to the gas to be measured, the other (e.g. by choosing an optical filter outside the absorption region) is insensitive to the gas to be measured, providing information on $I_o$ and its variations and enabling to correct for them. A drawback of a two channel system is the possibility of partial window shading, affecting only one of the channels, in which case the correction for $I_o$ will yield false results.

c) Optical Considerations.

Additional demands from some gas measuring instruments, e.g., mainstream $CO_2$ sensing units, are a fast response time and the need to minimize the possibility of obstructions in the cuvette which is part of the airway. This requires for aerodynamic reasons an optical path length of at least several mm. At prevailing $CO_2$-concentrations, a long optical path length may cause very high absorption. Therefore, there is need to "tailor" the absorption curve to be still responsive at these path lengths to high $CO_2$-concentrations. This will cause relative insensitivity at the low concentration edge with conditions of accidental rebreathing not being detectable with any reliability either in single or in two-channel systems.

Methods and devices are also known, both for medical and non-medical applications, that require the use of a reference gas. A serious disadvantage of these prior-art methods and devices resides in the fact that the concentrations of these references gases must not only be known, but must also remain constant with time.

It is thus one of the objects of the present invention to overcome the drawbacks and disadvantages of the prior-art methods and to provide a method for gas analysis that gives results not affected by window shading, that, over the entire measurement range, is sensitive also to lower concentrations and thus facilitates detection of accidental rebreathing, that does not require an exact knowledge, or indeed constancy, of a reference gas if used, corrects itself for zero drift and shows no cross absorption by $N_2O$ or other anesthetic gases.

According to the invention, this is achieved by providing a method for analyzing gases to establish their concentration, comprising the steps of:

a) providing a radiant source, an analytical space, a radiation detector and a reference gas having a concentration HC beyond the range of concentrations of the gas to be analyzed, b) establishing an instantaneous intensity $I_{LC}(t)$;

c) establishing an intensity $I_{HC}$ with said analytical space filled with said reference gas;

d) calculating, from said values $I_{LC}(t)$ and $I_{HC}$, the instantaneous value of the absorbed intensity $Abs(t)$; and e) translating said absorbed intensity $Abs(t)$ into concentration values.

The invention further provides a method for measurement of gas concentrations, comprising the steps of:

a) providing a radiant source, an analytical space and at least two radiation detectors representing separate yet interactive channels, a first channel sensitive to the entire range of pertinent concentrations and a second channel predominantly sensitive to lower concentrations;

b) establishing a reference intensity $I_{A(LC)}$ for said first channel A by measuring, using the detector of said first channel, intensity during periods of low concentrations (LC) only, and establishing a reference intensity $I_{B(HC)}$ for said channel B by measuring, using the detector of said second channel, intensity during periods of high concentrations (HC) only;

c) establishing, for said first channel A and by substantially continuous monitoring, an instantaneous intensity $I_A(t)$ and calculating, for each $I_A(t)$ value, a function $F[I_A(t), I_{A(LC)}]$, and establishing, for said second channel B and by substantially continuous monitoring, an instantaneous source intensity $I_B(t)$ and calculating for each $I_B(t)$ value, a function $F[I_B(t), I_{B(HC)}]$;

d) calculating from said function $F[I_A(t), I_{A(LC)}]$ the absorption values $Abs_A$ for said first channel A at each sampling instant t, and calculating from said function $F[I_B(t), I_{B(HC)}]$ the absorption values $Abs_B$ for said second channel B at each sampling instant t;

e) translating said absorption values $Abs_B$ into concentration values $Conc_B$, using a function $F_B$;

f) establishing the low-concentration values $Conc_{B(low)}$ on said channel B for calculation of a correction factor Z for said first channel A;

g) correcting said absorption values $Abs_A$ for said first channel A, using said correction factor Z as obtained from said second channel B;

h) translating said corrected absorption values $Abs_{Acorr}$ into corrected concentration values, $Conc_{corr}$, using a function $F_A$.

The invention still further provides a gas analyzer, comprising: a radiation source, an analytical space through which passes the gas to be analyzed, at least one detector for detecting the intensity of radiation passing through said space; means facilitating the alternating introduction, into said space, of said ga to be analyzed and a reference gas having a concentration located at least in the upper half of the range of concentrations to be measured by said gas analyzer; processing means, having memory means, to process signals originating in said detector, said memory means adapted to store in a first mode of operation signals representing instantaneous intensity values of the detected source and, in a second mode of operation, to store signals representing intensity values obtained when said analytical space is filled with said reference gas; circuit means for comparing said instantaneous values with said reference value; and indicator means for indicating concentration.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the mos useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 4:
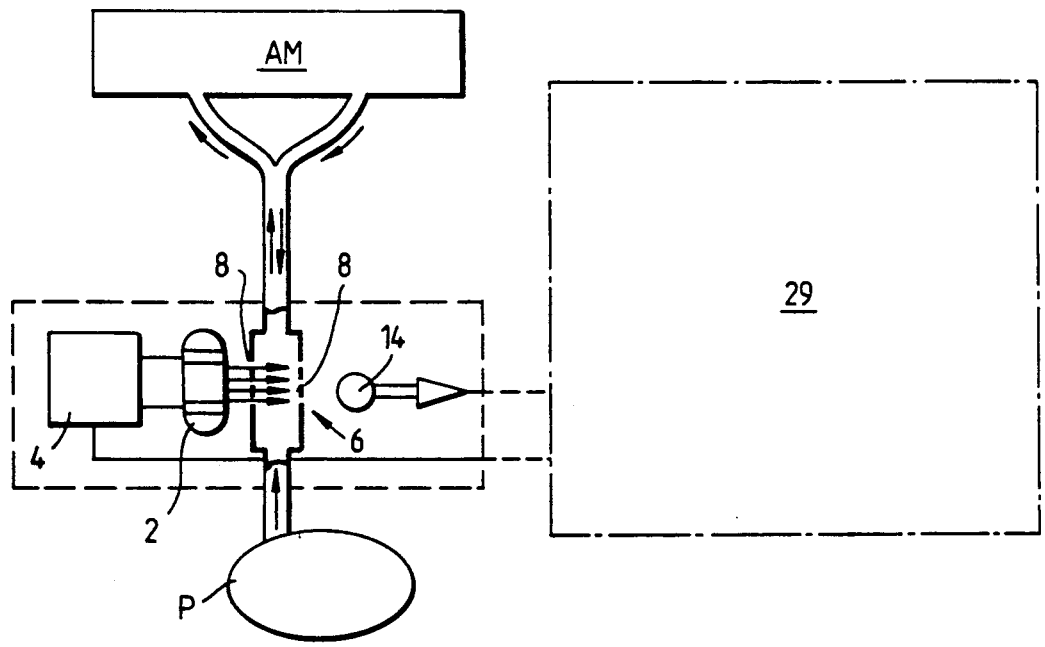
Figure 5:
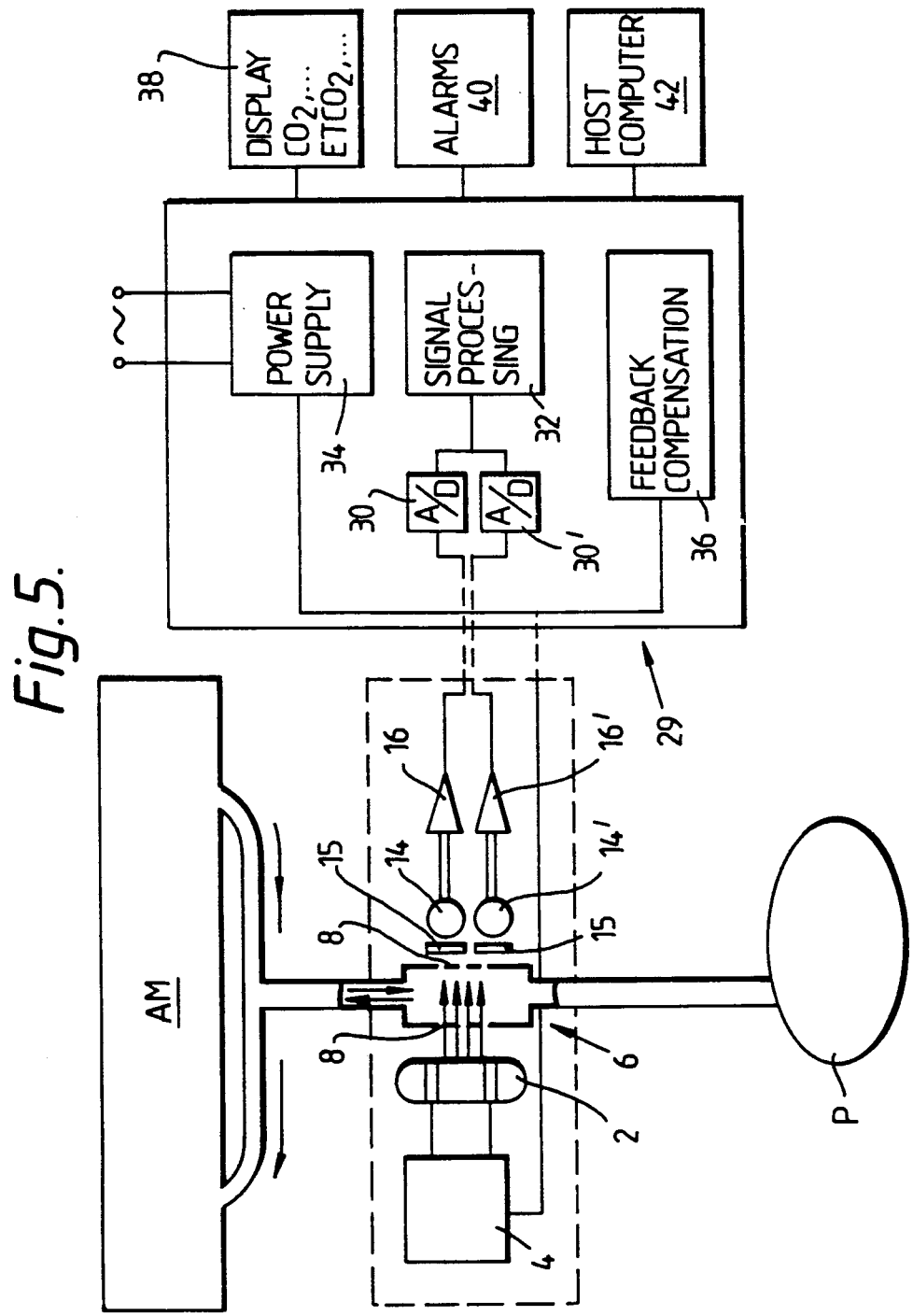
Figure 6:
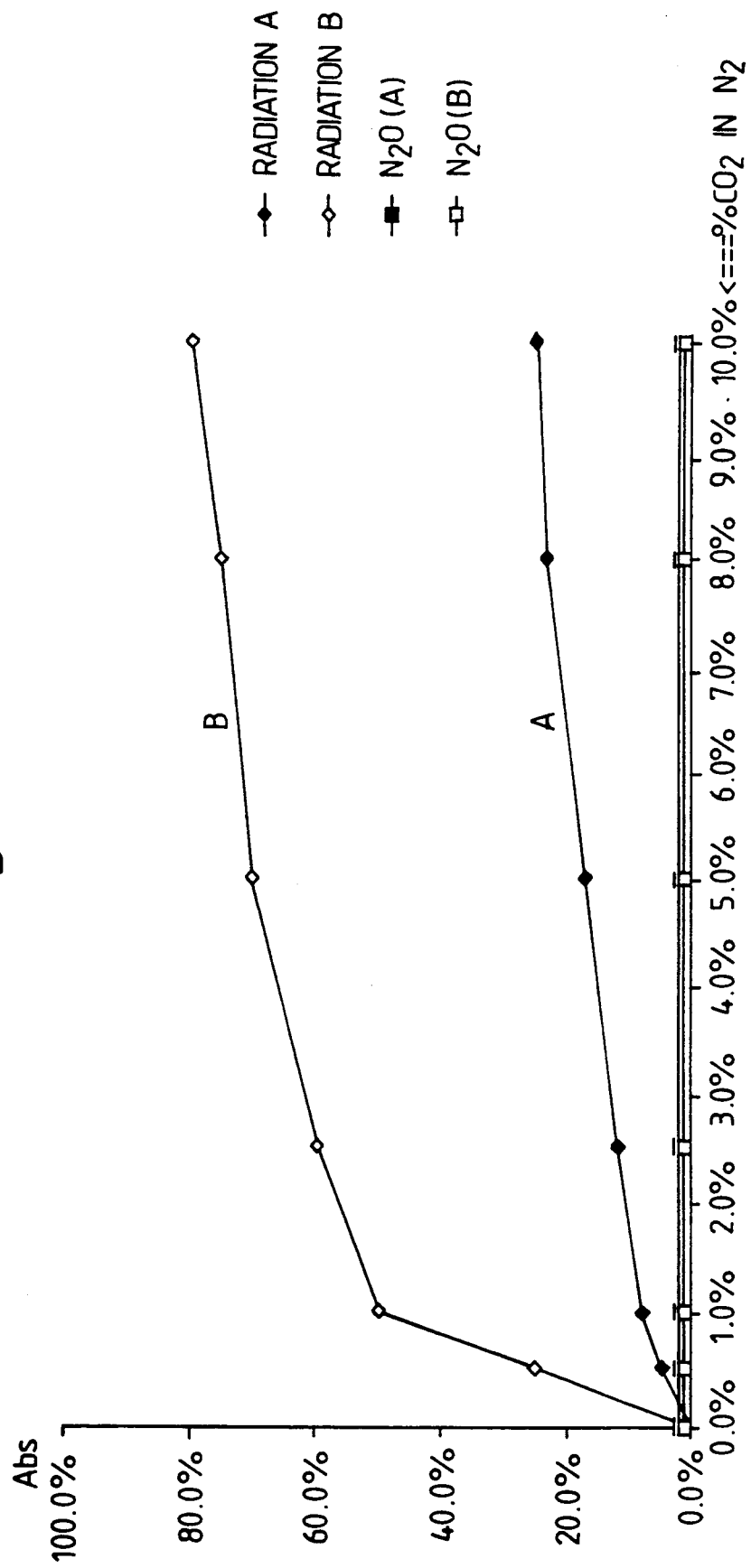

FIG. 4 schematically represents a gas analzyer according to the invention in conjunction with an anesthesia machine;

FIG. 5 illustrates another embodiment of the invention, which is adapted to function as a capnometer;

FIG. 6 shows absorption as a function of concentration for two different wave lengths; and FIG. 7 is a flow diagram representing the operational sequence of steps associated with the gas analyzer of FIG. 5.

Figure 1:
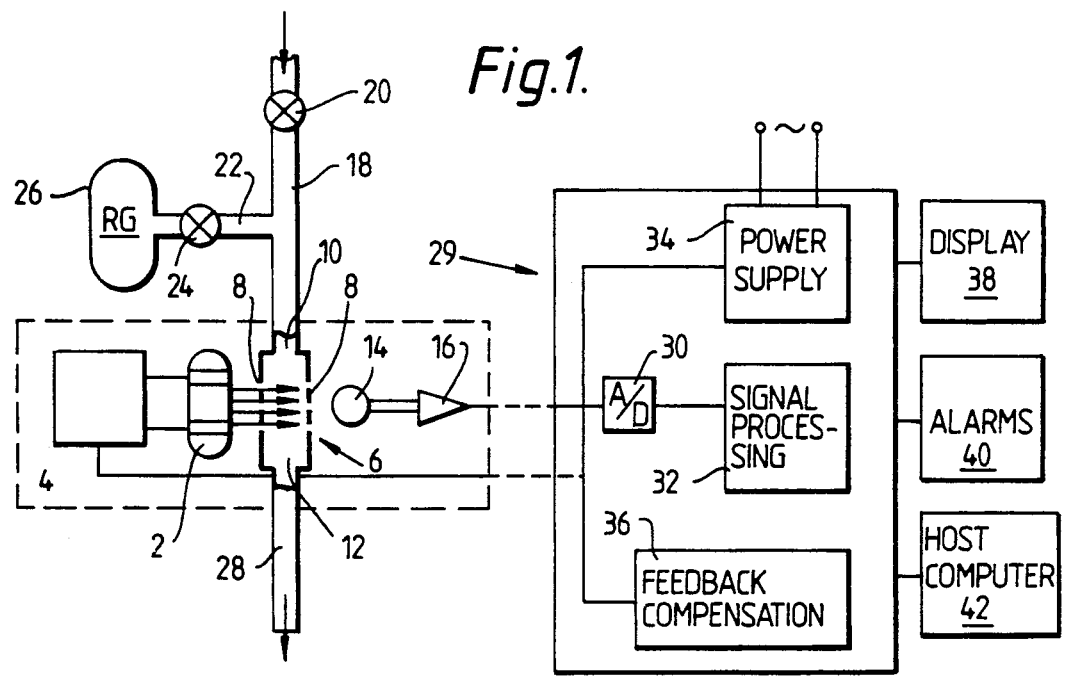
FIG. 1 is a schematic representation of a first embodiment of the gas analyzer according to the invention, to be used, e.g., to measure gas concentrations in closed spaces.

Referring now to the drawings, there is shown in FIG. 1 a radiation source 2 and its driver, in the form of a chopper or oscillator 4. The source 2 is an IR-emitter, such as, e.g., a black-body radiator, a specific molecular source or a laser, radiating at a wavelength or range of wave-lengths absorbable by the gas in question.

The radiation produced by the source 2 passes through the analytical space in the form of a cell or cuvette 6 having two windows 8 made of a material transparent to the radiation emitted by the source 2, and is partly absorbed during this passage by the gas. In a way to be explained further below, this absorption is determined and constitutes a measure of the prevailing concentration.

The cuvette 6 has an inlet opening 10 through which enters, drawn or pushed, e.g., by a pump (not shown) the gas to be analyzed, and an outlet opening 12 through which the gas can leave the cuvette 6.

Further seen inside the instrument housing denoted by broken lines, is a radiation detector 14 associated with a preamplifier 16.

Outside of the housing there is seen a supply tube 18 attachable to the cuvette inlet opening 10, a first valve 20 adapted to close off the supply tube 18, a tube 22 branching off the supply tube 13 and leading, via a second valve 24, into a vessel 26 containing a reference gas RG. The gas exits the cuvette 6 through a tube 28.

The electronics 29 of the device are seen on the right and comprise an analog/digital converter 30 feeding the signal-processing unit 32 which carries out the method steps described further below, a power supply 34 feeding all components, including the oscillator 4 and a feedback compensator 36. As peripherals serve a display 38, an alarm 40 and a host computer 42.

Figure 2:
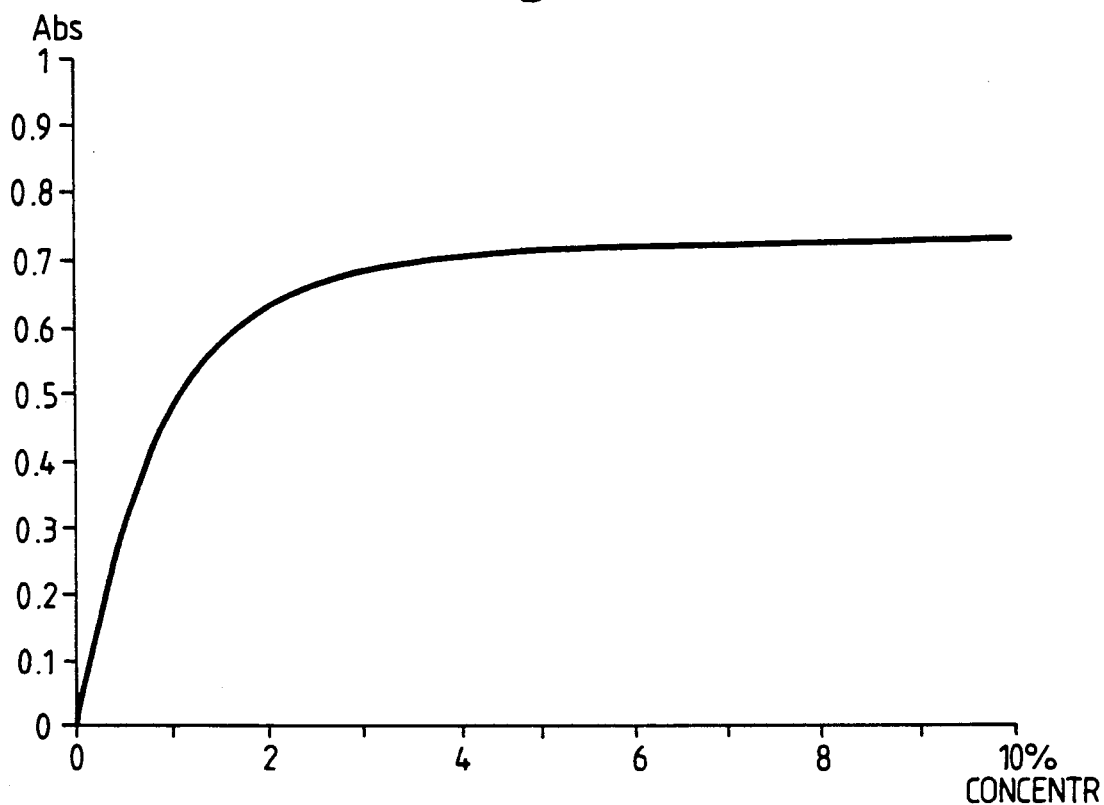
FIG. 2 is a diagram, representing absorption as a function of concentration.

A typical absorption curve, i.e. a curve representing absorption as a function of gas concentration, is shown in FIG. 2. The curve is seen to have two distinctly different portions: a first, steep and substantially linear portion in which absorption is non-saturated, and a second, rather flat portion, in which absorption is substantially saturated, i.e., in which increases in concentration will produce only very slight increases in absorption and thus, very slight decreases in radiation intensity.

The reference gas RG has a concentration substantially higher than the concentration of the full measuring range.

Absorption by this gas RG is saturated, only slightly depending on exact gas concentration. The intensity impinging on the detector 14 is $I_{RG}$ or, in the notation used farther below, $I_{HC}$ (for high concentration). This value is a fairly constant percentage $Y_o$ of the nonabsorbed intensity $I_o$ (in the present example $Y_o$ is about 28% of $I_o$) and can therefore be used as reference value to calculate absorption in the measuring range.

Figure 3:
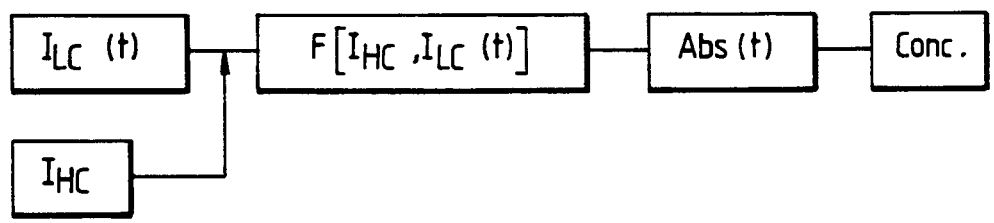
FIG. 3 is a flow diagram representing the operational sequence of steps associated with the gas analyzer of FIG. 1.

The operational sequence of this embodiment is graphically illustrated in FIG. 3. After determining the instantaneous intensity value $I_{LC}(t)$ (at the prevailing low concentration LC) and, as part of the processor routine, having it stored in the processor memory, the valve 20 is closed and the valve 24 opened (either manually if referencing need be carried out at relatively long intervals, or automatically as controlled by a program). As a consequence, the analytical space, i.e., the cuvette 6 is no filled with the reference gas RG, the concentration HC of which, although not necessarily known to any degree of accuracy, must be beyond the possible range of concentrations of the gas to be analyzed, in fact must be high enough to produce saturation of absorption.

With the cuvette 6 now containing the high-concentration reference gas, $I_{HC}$ is determined and stored.

Next, the processor calculates the function $F[I_{HC}, I_{LC}(t)]$, from which, in a further step, the instantaneous value of the absorbed intensity Abs(t) is calculated which, in a final step, is translated into concentration values. This translation is thus based on the knowledge of intensity in the state of saturation, and is therefore independent of its actual concentration (provided the latter is high enough, as stated), while prior-art instruments measure the reference gas, amongst other methods, in a state of unsaturated absorption, therefore, requiring knowledge of its exact concentration.

While FIG. 1 shows the reference gas as being contained in a bottle, to be added at predetermined intervals, the reference gas may also become available as the natural result of periodic variations in concentration of the gas to be analyzed. It is also possible to introduce a reference gas through the tube 18. Thus, an attendant in an underground parking garage in which CO concentration is monitored, may use a hose connected to the exhaust pipe of a car to introduce exhaust gas. For $CO_2$ monitoring, he could in fact blow into tube 18, making use of his exhalation air (about 5% $CO_2$) as reference gas.

FIG. 4 shows an embodiment similar to the embodiment of FIG. 1 (but without the reference-gas bottle) working in conjunction with an anesthesia machine AM through which the patient P breathes. He exhales into the machine which, by "scrubbing", removes the $CO_2$ and is supposed to return to him $CO_2$-free air plus appropriate doses of an anesthetic agent. A major purpose of the gas analyzer according to the invention is in this case the immediate detection of $CO_2$-rebreathing in case of malfunction of the machine.

Here, the exhalation air of the patient ($CO_2$-concentration about 5%) serves as reference gas producing saturated absorption. The relative intensity $I_{HC}$ of the radiation passing this "reference gas" is, for all practical purposes, constant and serves as reference value for the calculation of the above-mentioned absorption Abs(t) during inhalation. Should a drastic change appear in the ratio between the inhalation signal and the exhalation signal, this would indicate a situation of rebreathing, actuating the alarm 40 (FIG. 1), Another embodiment of the gas analyzer according to the invention is seen in FIG. 5, to be used as a capnometer, a device for analyzing breath, mainly, though not exclusively, for $CO_2$.

This embodiment differs from the previous ones in that it has two detectors 14, 14, ' as well as two different filters 15, 15', the detectors representing two separate but, as will be seen, interactive channels A and B.

The radiation source may be a black-body radiator a specific molecular source or a laser, in any case a source that emits two different, mostly closely spaced, wavelength bands, both of them absorbed by the gas to be analyzed.

Particularly advantageous for $CO_2$ measurement were found specific molecular discharge sources containing, for example, either $^{12}CO_2$ and/or $^{-}CO_2$ and/or $C^{18}O_2$ as active gases. As to the filters, good results were obtained with a channel A filter transmitting in a range between 4.0 and 4.4 pm, and with a channel B filter transmitting in a range between 4.2 and 4.6 $\mu m$.

As a consequence, each of the detectors 14, 14' due to their particular filter 15 and 15', respectively, "sees" radiation of a different wavelength. Now, since the absorption coefficient in the Beer-Lambert Law is wavelength-dependent: $k = k(\lambda)$, it is clear that different absorption curves will be obtained.

FIG. 6 shows such a possible pair of absorption curves. Due to a judicious choice of radiation source and filters 15, 15', the following characteristics are obtained:

The curve of channel A is non-saturated and fairly linear and, due to its relative flatness, will produce weak changes in the signal with changing $CO_2$-concentration, while the curve of channel B has a steep slope, i.e, high sensitivity in the lower concentrations, while indicating less sensitivity in the higher concentrations, where the absorption is largely saturated.

Also shown are curves related to such anesthetic gases as $N_2O$. The shape and location of these curves indicate the substantial absence of cross absorption.

The following is an explanation as how this "two-channel, two-absorption curves" arrangement can be utilized as referencing system, where each channel acts as a reference for the other.

The weakly absorbed, more linear, channel A will be used to monitor the patient's $CO_2$-concentration. In medical $CO_2$-monitoring, the region of the so-called end-tidal $CO_2$ concentration ($ETCO_2$) of, normally, around 5% is of most clinical interest. This is where channel A is most sensitive, therefore, it will be called "Measuring Channel".

During the breathing cycle, the output of detector 14 (channel A) will change typically from maximal output $I_A$ to 0.80 $I_A$ cycling between these values. During the same breathing cycle the output of detector 14' (channel B) will change from $I_B$ to 0.3 $I_B$.

Channel A is essentially a single independent channel—changes in source intensity and also in window shading will be corrected by the knowledge that during inhalation (or flow of zero gas in other applications), the intensity measured is $I_{A(o)}$, e.g., $I_A$ (inhalation) = $I_{A(o)}$ and absorption is calculated in reference to $I_{A(o)}$: $Abs_A = [(1 - I_A/I_{A(o)}]$.

This referencing is accurate as long as the concentration of the zero gas is guaranteed indefinitely. But in conditions of rebreathing, this is not the case. It is therefore necessary to be able to monitor sensitively the period of inhalation for the presence of $CO_2$. Highly sensitive measurement of inhalation is effected by Channel B. Since during exhalation, the common end-tidal $CO_2$ concentrations are around 5%, the signal will be strongly diminished but remains substantially unaffected by variations in the 3%–10% range. This exhalation signal may be regarded as the "base line" for the inhalation stage, where small changes in $CO_2$ concentration will extremely affect the signal level and therefore the $I_o$ (inhalation)/$I_o$(exhalation) ratio. Therefore, channel B becomes effectively a "one source, single-path, single-detector system". Its "zero-gas" reference is the saturation signal with the attributes mentioned above.

This "reference channel B" will be used to correct the base line of the "Measuring channel A" against errors as in the case of rebreathing.

It is clear from this description that every channel is independent regarding problems of partial window shading. This is not the case in prior art, where channel B serves as base line for calculating the absorption in channel A, where partial window-shading will lead to appreciable error.

To enhance accuracy of the proposed method, the knowledge of the ETCO2 concentration calculated from channel A can be used to correct channel B in second order.

FIG. 7 represents the sequence of steps associated with the operation of the gas analyzer of FIG. 5. It should be noted that in order not to tie down this embodiment to its use as capnometer, terminology and subscripts have been generalized. Thus, the intensity measured in channel A during periods of "zero gas" inhalation only is subscripted A(LC) rather than A(O), and the exhalation values of channel B will be subscripted B(HC), LC and HC standing for low and high concentration, respectively.

As a first step, a reference intensity $I_{A(LC)}$ is established in channel A by using the detector 14 to measure the intensity during periods of low concentrations (LC) only. Similarly, a reference intensity $I_{B(HC)}$ is established in channel B by using the detector 14' to measure the intensity during periods of high concentrations (HC) only.

Next, after having determined, by substantially continuous sampling, an instantaneous intensity $I_A(t)$ for channel A, a function $F[I_A(t), I_{A(LC)}]$ is calculated for each $I_A(t)$ value. Then, analogously, having determined, by substantially continuous sampling, an instantaneous intensity $I_B(t)$ for channel B, a function $F[I_B(t), I_{B(HC)}]$ is calculated for each $I_B(t)$ value, and modified with a constant $Y_o$ defined by the characteristics of the system.

Subsequently, the absorption $Abs_A$ at each sampling instant t is calculated for channel A from the function $F[I_A(t), I_{A(LC)}]$ and, similarly, the absorption $Abs_B$ at each sampling instant t is calculated for channel B from the function $F[I_B(t), I_{B(HC)}]$.

The absorption values $Abs_B$ are then translated into concentration values $Conc_B$, using a function $F_B$ established at the factory and updated and slightly corrected during periodical calibration of the device.

The low-concentration values $Conc_{B(low)}$ on channel B are now established to calculate a correction factor Z for channel A, using a function $F_A$ established at the factory and updated and slightly corrected during periodical calibration of the device.

Finally, Z is used to correct the absorption values $Abs_A$ for channel A.

For even greater accuracy and in cases where saturation in channel B is possibly less than full, the high-concentration periods on channel A $Conc_{A(high)}$ can be used to calculate a further, second-order correction factor, Y, to be applied to channel B in order to modify the above-mentioned correction factor Z, provided the successive mutual corrections have a converging character.

In order to allow for variations between different sensors and for zero drift during sensor life, calibration is required from time to time. The calibration procedure is used to modify the above-mentioned factory-established correlation functions between absorption and concentration.

Calibration, e.g., of the two-point type, is carried out, e.g., with cells containing a gas of known concentration (zero and span) or by having a known gas flow through the cuvette 6.

With the device of FIG. 5 used as a capnometer, the high-concentration values obtained in channel A also permit the calculation of the earlier mentioned end-tidal $CO_2$ values (ETCO2), of considerable importance as a diagnostic tool.

It is entirely possible to add a third channel, C, to determine concentrations of a second gas, e.g., $N_2O$, using the radiation emitted by the same source. The procedure is similar, except that the reference intensity is established during calibration and that correction factors have to be used for window shading and source-intensity fluctuations.

While the embodiment of FIG. 5 is shown in association with an anesthesia machine, it will obviously work also with, e.g., a ventilator, or without either of these machines.

It will be appreciated that multiple-wavelength emission is achievable also by means other than those mentioned.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for analyzing gases to establish their concentration, comprising the steps of:
    a) providing a radiant source, an analytical space, a radiation detector and a reference gas having a concentration HC beyond the range of concentrations of the gas to be analyzed,
    b) establishing an instantaneous intensity $I_{LC}(t)$;
    c) establishing an intensity $I_{HC}$ with said analytical space filled with said reference gas;
    d) calculating, from said values $I_{LC}(t)$ and $I_{HC}$, the instantaneous value of the absorbed intensity Abs(t), and
    d) translating said absorbed intensity Abs(t) into concentration values.

2. A method for measurement of gas concentrations, comprising the steps of:
    a) providing a radiant source, an analytical space and at least two radiation detectors representing separate yet interactive channels, a first channel sensitive to the entire range of pertinent concentrations and a second channel predominantly sensitive to lower concentrations;
    b) establishing a reference intensity for said first channel A by measuring, using the detector of said first channel, intensity during periods of low concentrations (LC) only, and establishing a reference intensity $I_{B(HC)}$ for said channel B by measuring, using the detector of said second channel, intensity during periods of high concentrations (HC) only;
    c) establishing, for said first channel A and by substantially continuous monitoring, an instantaneous intensity $I_A(t)$ and calculating, for each $I_A(t)$ value, a function $F[I_A(t), I_{A(LC)}]$, and establishing, for said second channel B and by substantially continuous monitoring, an instantaneous source intensity $I_B(t)$ and calculating for each $I_B(t)$ value, a function $F[I_B(t), I_{B(HC)}]$;

d) calculating from said function $F[I_A(t), I_{A(LC)}]$ the absorption values $Abs_A$ for said first channel A at each sampling instant t, and calculating from said function $F[I_B(t), I_{B(HC)}]$ the absorption values $Abs_B$ for said second channel B at each sampling instant t;

e) translating said absorption values $Abs_B$ into concentration values $Conc_B$, using a function $F_B$;

f) establishing the low-concentration Values $Conc_{B(low)}$ on said channel B for calculation of a correction factor Z for said first channel A;

g) correcting said absorption values $Abs_A$ for said first channel A, using said correction factor Z as obtained from said second channel B;

h) translating said corrected absorption values $Abs_{Acorr}$ into corrected concentration values, $Conc_{corr}$, using a function $F_A$.

3. The method as claimed in claim 2, comprising the further steps of using the values obtained during high-concentration periods on said first channel A to determine $Conc_{A(high)}$ for calculation of a correction factor Y for said second channel B, said correction factor Y to be used to modify said correction factor Z, provided the successive mutual corrections have a converging character.

4. A gas analyzer, comprising:
a radiation source;
an analytical space through which passes the gas to be analyzed;
at least one detector for detecting the intensity of radiation passing through said space;
means facilitating the alternating introduction, into said space, of said gas to be analyzed and a reference gas having a concentration located at least in the upper half of the range of concentrations to be measured by said gas analyzer,
processing means, having memory means, to process signals originating in said detector, said memory means adapted to store in a first mode of operation signals representing instantaneous intensity values of the detected source and, in a second mode of operation, to store signals representing intensity values obtained when said analytical space is filled with said reference gas;
circuit means for comparing said instantaneous values with said reference value, and
indicator means for indicating concentration.

5. The gas analyzer as claimed in claim 4, wherein said radiation source is a black-body radiator.

6. The gas analyzer as claimed in claim 4, wherein said radiation source is a specific molecular discharge source.

7. The gas analyzer as claimed in claim 4, comprising at least two detectors.

8. The gas analyzer as claimed in claim 4, wherein said radiation source emits radiation of at least two different wavelengths or wavelength bands, both absorbable by said gas to be analyzed.

9. The gas analyzer as in claim 7 or 8, comprising a filter for each of said at least two detectors, said filters being interposed between said analytical space and the respective detectors, each filter substantially transmitting a different one of said at least two wavelengths or wavelength bands.

10. The gas analyzer as claimed in claim 4, wherein the concentration of said reference gas is beyond the range of concentrations to be measured by said gas analyzer.

* * * * *

UNITED STATES PATENT AND TRADEMARK OFFICE
CERTIFICATE OF CORRECTION

PATENT NO. : 5,063,275

DATED : November 5, 1991

INVENTOR(S) : Elieser Zwi Rosenfeld, et al.

It is certified that error appears in the above-identified patent and that said Letters Patent is hereby corrected as shown below:

Column 3, line 25: "ga" should read as --gas--

Column 3, line 48: "mos" should read as --most--

Column 5, line 4: "no" should read as --now--

Column 8, line 59, Claim 2: "intensity for" should read as --intensity $I_{A(LC)}$ for--

Signed and Sealed this

Sixteenth Day of March, 1993

*Attest:*

STEPHEN G. KUNIN

*Attesting Officer*     Acting Commissioner of Patents and Trademarks